United States Patent [19]

Treace

[11] 4,288,066
[45] Sep. 8, 1981

[54] CONTAINER FOR MEDICAL DEVICE

[75] Inventor: Harry T. Treace, Forest Hill, Tenn.

[73] Assignee: Richards Manufacturing Company, Inc., Memphis, Tenn.

[21] Appl. No.: 101,773

[22] Filed: Dec. 10, 1979

[51] Int. Cl.$^3$ .............................................. B25B 1/24
[52] U.S. Cl. ................................... 269/270; 269/287; 269/307; 269/909; 206/210; 206/459; 220/339
[58] Field of Search .................... 269/287, 289 R, 307, 269/270, 295, 302.1, 909; 128/1 R; 206/210, 459; 220/339, 375; 33/487, 483, 174 B, 174 G

[56] References Cited

U.S. PATENT DOCUMENTS

| | | | |
|---|---|---|---|
| 4,050,975 | 9/1977 | Draffone | 269/295 X |
| 4,124,151 | 11/1978 | Hazard | 220/339 X |
| 4,169,531 | 10/1979 | Wood | 220/339 X |

*Primary Examiner*—Robert C. Watson
*Attorney, Agent, or Firm*—Robert D. Yeager

[57] ABSTRACT

The present invention provides a container, package, or case and at the same time an article of surgical equipment for the storage, transportation, asepsis and surgical preparation of a medical device. The container is especially adapted for small, delicate, otic prostheses, the type used as a middle ear implant, such as a total or partial ossicular replacement prosthesis. The container comprises a base that constitutes a work area and has a first recessed area formed therein conforming to the shape and size of the prosthesis which it will carry. The end of this first recessed area opens laterally into a contiguous, coplanar second recessed area adapted in cooperation with the said work area to use in preparation of the prosthesis. Disposed on the base opposite the second recessed area and parallel to the longitudinal axis of the first recessed area are measuring apparatus having a scale set perpendicular to the said longitudinal axis. A raised cutting platform adapted to cutting cartilage, tissue or fascia, is disposed on the base so as to be enclosed within the case when the lid is closed. On the inside of the lid of the container, immediately opposite the prosthesis-holding recessed area of the base is a complementary recessed portion.

5 Claims, 6 Drawing Figures

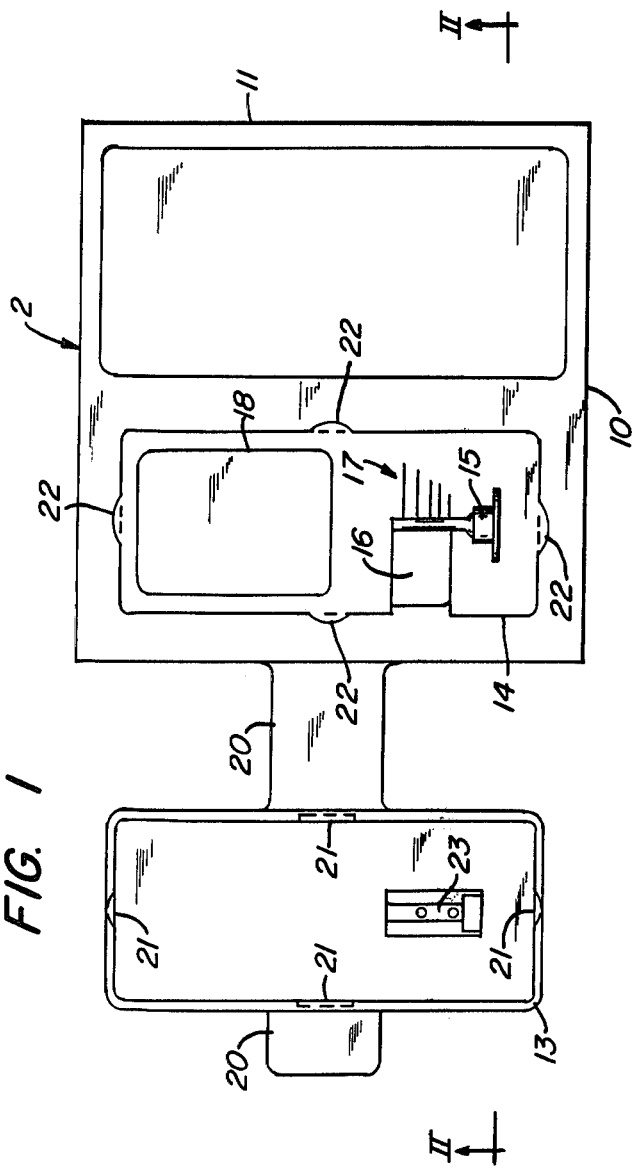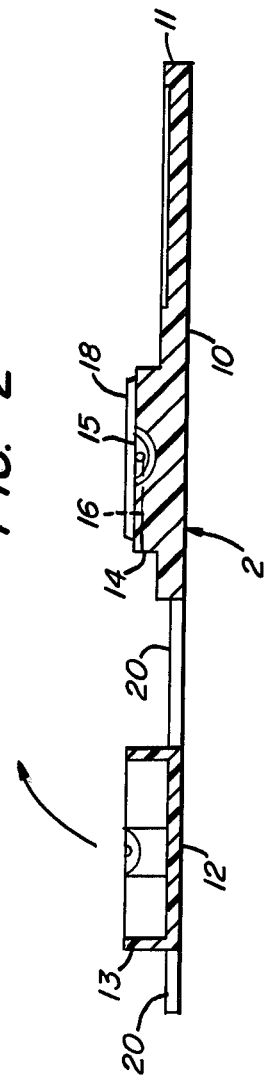

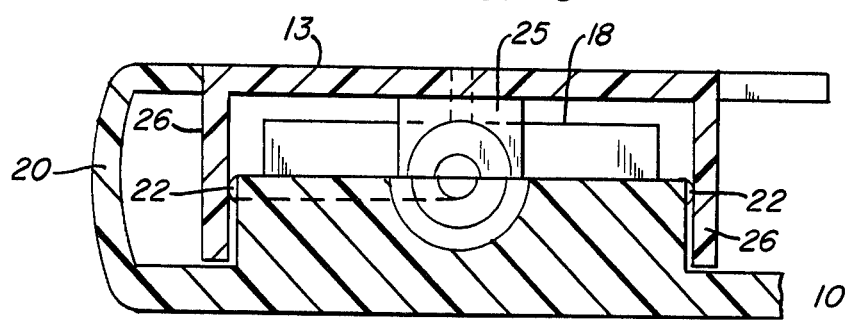
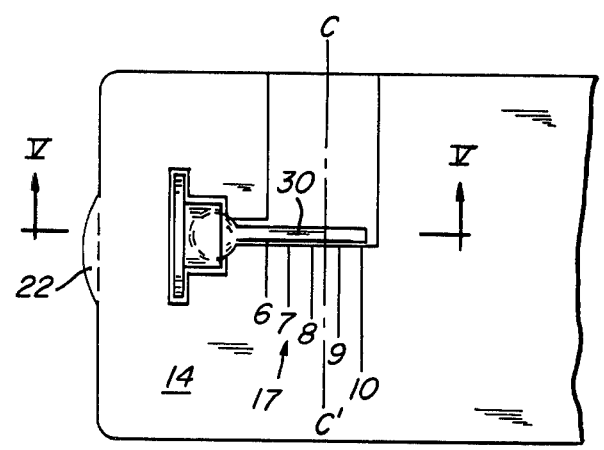
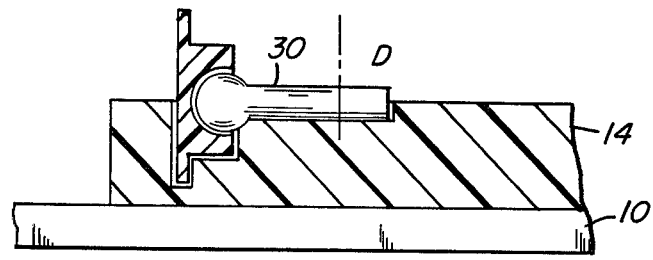

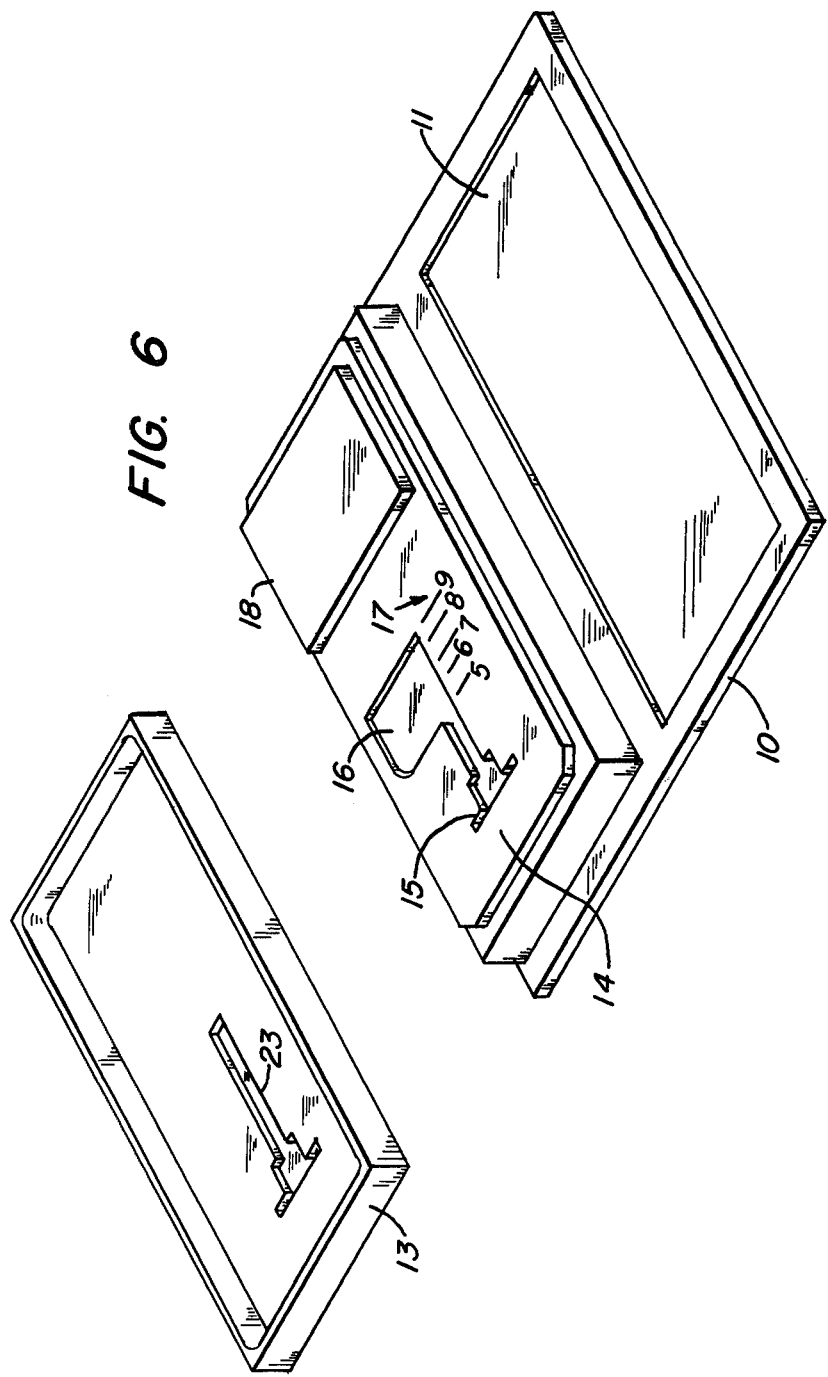

CONTAINER FOR MEDICAL DEVICE

CROSS REFERENCE TO RELATED APPLICATIONS

This application is related to U.S. Ser. No. 101,774, filed concurrently herewith, entitled "Middle Ear Ossicular Replacement Prosthesis Having a Movable Joint", assigned to the assignee hereof.

BACKGROUND OF THE INVENTION

1. Field Of The Invention

This invention relates to containers for medical devices, e.g., those for prostheses, and specifically to containers for those prostheses which are designed for use as implants in the middle ear. These small and delicate prostheses are designated as ossicular replacement prostheses and are used in replacing some or all of the small bones of the middle ear in reconstruction of its sound-conducting mechanisms. The present invention relates also to surgical aids useful during the procedure of the implantation of such prostheses.

2. Description Of The Prior Art

In containers for prostheses and other related medical equipment, molded synthetics have been used having cavities or depressions to accommodate the equipment, and the containers have been provided with snap-on type lids. Some equipment cases, such as those of the assignee, Richards Manufacturing Co., Inc., for bone screws, contain an indication of the length of the device. These cases are used to hold the device during shipping and storage, and may also be used as the container during disinfection or sterilization when made of suitable material to withstand the process.

A prosthesis, for example of the type used in the middle ear, when received in sterile or aseptic condition in its case in the surgical theater, may then be removed from the case to be measured, sized, grafted and/or cut as required for the particular surgery being performed. Considering the delicate structure and small size of such prostheses, there are hazards inherent in removing the prothesis from its case, and cutting it to a carefully predetermined size or otherwise preparing it and associated tissue for its implantation. Among those hazards are damage to and contamination of the prosthesis, and occasionally loss of the device itself.

SUMMARY OF THE INVENTION

This invention proposes a container and surgical aid that can accommodate all the transportation and processing requirements of a medical device from its initial manufacture until its final utilization, including actual implantation in surgery.

The container comprises a base which serves as a work area and has recessed therein a first recessed area or holding cavity conforming to the shape or size of the device or prosthesis which it will carry. The first recessed area has a lateral and longitudinal axis accommodating to the shape of the device. One end of this first recessed area opens laterally into a second recessed area, a contiguous coplanar trim cavity that in combination with the said first recessed area is adapted for preparation of the device for use, such as cutting the shaft of a middle ear prosthesis, as it remains in the first recessed area, to the correct length for the ear of the individual patient. Disposed integrally on the base opposite to the second recessed area and adjacent to the first recessed area are measuring means for use in preparation of the device, for example the said cutting of the shaft of a middle-ear prosthesis. The precise geometry of the said first recessed area formed in the base and accommodating the prosthesis and of a complementary recess or holding fixture formed on the inside of the lid of the container firmly secures the device and prevents motion within the closed container that might otherwise damage or dislodge the device, especially a delicate prosthesis.

It is to the protection of such delicate prostheses as those for implantation in middle-ear surgery that the container is particularly adapted. The portion of the first recessed area holding the head of such a middle-ear prosthesis will form a semi-circular depression in the base. This will effectively hold in place the top or head portion, as well as the upper shaft, of the prosthesis. The said depression, coupled with the complementary lid portion, when closed, will prevent any lengthwise or back-and-forth motion of the implant within the recessed base of the container even though the prostheses themselves are small with respect to the necessary clearances of the surrounding packaging. An extension of the base of the container and surgical aid will be sufficiently wide and long to lend stability to the entire container as it is employed in the critical, necessarily highly accurate cutting to size of the prosthesis and also of tissue to be employed in the surgical implantation. Enclosed within the lid portion, when the container is closed, is also a cutting platform or work table for the tissue grafts associated with the implantation of the prosthesis in the middle ear. The cutting platform may also be provided with measuring means.

The prosthesis can thus not only be stored, shipped and disinfected or sterilized within the container and surgical aid but also the necessary sizing and surgical preparation (such as prosthesis or tissue graft cutting) may be performed on or within it. It is, therefore, not necessary for the surgeon to remove the prosthesis from the container to measure and cut the prosthesis to size, or to perform in his hands the tissue graft cutting required in ossicular replacement surgery. The precise geometry of the depression or holding cavity within the container accommodating the prosthesis and of the complementary structure of the lid portion is especially salient in light of the extremely small size of ossicular replacement prostheses relative to the size of necessary clearances between the prostheses and their containers. Thus, in the described and illustrated embodiment, there are combined with the retaining cavities of the case and lid portion an integral measuring device and associated trim cavity for cutting the prosthesis in place to the precisely required size and a work table for cutting tissue also to appropriate size for associated implantation with the prosthesis. Additional desirable features are described in the subsequent further description of a preferred embodiment.

BRIEF DESCRIPTION OF THE DRAWINGS

The drawings accompanying this application and illustrating a preferred embodiment of the device of invention consist of the following Figures:

FIG. 1 is a plan view of the container and surgical aid of the present invention showing one selected means (a flexible plastic strip) by which the cover portion is hinged or attached to the base;

FIG. 2 is an elevational view taken along lines II—II of FIG. 1;

FIG. 3 is a cross-sectional end view of the container with parts broken away and showing the complementary fit of the cover portion which provides stability to and protection of the contained prosthesis;

FIG. 4 shows in some detail an enlarged plan view, with parts broken away, of the holding recess, measuring means, and trim cavity of the container;

FIG. 5 shows in some detail an enlarged vertical section of that portion of the container shown in FIG. 4 and taken along lines V—V of that figure; and FIG. 6 shows a perspective view of the container with the cover portion or lid of the container being shown, for purpose of clarity, somewhat removed from the base.

DESCRIPTION OF THE PREFERRED EMBODIMENTS

Referring to FIGS. 1 and 2, the container and surgical aid of this invention is designated by the general reference numeral 2. There is shown a base 10 including an extended area 11 to provide stability to the container 2 which may include a slightly raised or depressed area for affixation or imprinting of a label or instructions for use of the medical device carried therein. Similarly the top surface 12 (when closed) of the lid 13 can bear a label or be imprinted or embossed. A raised work area 14 of the base 10 contains the receptacle for a prosthesis, provided by a depressed area or cavity 15 in the said work area 14, the depressed area 15 conforming to the geometry of the prosthesis to be enclosed in the device. A second depressed area 16 extends laterally from one side of the first depression 15 and provides a trim cavity for cutting the shaft of the prosthesis. Disposed opposite to the second depressed area 16 and longitudinally along the first depressed area is an embossed or imprinted scale 17 which in the present instance is subdivided into millimeters and denoted by attached or embossed numbers.

Directly associated with the depressed areas for holding the prosthesis and the work area 14 is a further work table or elevated cutting platform 18 for the preparation and sizing of a vein or tissue graft to be used in the surgical implantation of the prosthesis. The platform 18 may also be imprinted or embossed in either or both length and width to assist in sizing tissue grafts. The container as shown in the FIGS. 1 and 2 is provided with a flexible tab 20 integrally molded with the base 10 and extending from that side of the base containing work area 14. Molded to the tab 20 is the lid 13. The lid 13 and work area 14 are conventionally provided with molded recesses 21 and projections 22, respectively (see FIG. 1), to permit the lid 13 to snap in place on work area 14 when the tab 20 and lid 13 thereon are bent in the direction indicated by the arrow on FIG. 2. The lid 13 being provided by a complementary recess 23 will, when so bent over and fastened to work area 14, effect a closely fitting closure over the packaged prosthesis. As shown in FIG. 3, there can, in addition, be molded in the lid 13 a holding device 25 to secure the prosthesis along its shaft near its base. In FIG. 3 the tab 20 is shown schematically in bent position and the lid 13 is shown in place over the prosthesis. In that form of the container device shown in FIG. 3 clearance for the work table 18 is provided by the box shape of the lid 13 and its vertical sides 26.

An example of the cutting means that is provided by the present invention is shown diagrammatically in FIG. 4 in which a flexible prosthesis 30 of the type disclosed and claimed in copending application Ser. No. 101,774 is shown in place with the lid removed as would be the case when the container is being used in the operating room. Should, for example, the implantation require a prosthesis of 8.5 mm in length, the prosthesis 30 can be cut to size by the surgeon along lines C—C', before the device is removed for insertion.

In the Section V—V of FIG. 4 that is shown in FIG. 5, a prosthesis 30 in place is shown to extend above the first depressed area or holding cavity 15, and the cut C—C' is here shown in elevation D—D'.

In the perspective drawing of the container and surgical aid shown in FIG. 6 the complementarily recessed lid 13 thereof is shown removed from the base 10 and can in fact be conventionally fitted with molded edges 21 and tabs 22 (shown in FIG. 1) for snap fitting the cover portion over the base. The cover lid and base 10 can also be fitted with hinges or other conventional means for connecting the lid to the base so that the complementary recess or cavity 23 within the lid 13 and enclosed by the vertical sides 26 is precisely aligned to the first recessed area 15.

The container 2 of the present invention when sterilized and enclosing a prosthesis, is, as is conventional for devices intended for the operating room, enclosed and sealed in a transparent, plastic envelope, e.g., a sterilizing pouch.

One specific example of the invention as described is a custom storage, shipping, sterilizing, and cutting-platform container and surgical aid 2 for special types of middle ear prostheses, which contains cut-outs or depressions 15 and 23 custom-fitted to the geometry of the implant to minimize stress and damage to the delicate implants while in storage or transit, or while the prosthesis, or implant, is being cut to the appropriate length to fit an individual patient's ear. The work area 14 of the tray in the base of the container has embossed thereon a measuring scale 17 perpendicular to the longitudinal axis of the implant, and a trim cavity 16 on the opposite side of the longitudinal axis of the implant to enable the surgeon to insert a surgical knife, scalpel or razor blade to cut the implant to the desired length. The scale 17 has molded-in raised lines and letters to indicate the measurement for the implant. The work area 14 of the novel container also has a raised work table 18 which is useful to cut cartilage, tissue or fascia to the desired size for placement into the oval window of the middle ear or on the tympanum of the ear as a graft and seal. On the raised work table 18 there can be embossed additional scales and numbers indicating units of measurement (here, millimeters) preferably in both horizontal directions.

The container and surgical aid 2 including a lid 13, base 10, and work table 18 preferably will be in a flat dull color such as dark green or dark blue to reduce glare when the device is used in the surgical theater. In the lid 13 immediately opposite the holding cavity 15 of the base, which receives the implant, will be a matching recess or means 23 to fit over the implant, the latter incorporating a holding fixture (25 in FIG. 3) to grasp the upper half of the straight shaft of the implant to prevent vertical motion during transit or handling.

The container and surgical aid can be molded of synthetic resins which are sterilizable by gas or by treatment in an autoclave, provided that the prosthesis itself can withstand the particular type of sterilization.

While the container as shown is made to accommodate a single medical device or middle-ear prosthesis, multiple devices may be provided for in the container, the number of such items clearly not requiring provision therefor extending beyond the scope of the invention.

What is claimed is:

1. A container and surgical aid for the storage, transportation, asepsis and surgical preparation of a medical device, comprising:

a base comprising a raised platform adapted for preparing tissue utilized in implantation of said medical device, said base having a first recessed area adapted by size and shape to receive and conform to a substantial portion of said medical device, and a second recessed area coplanar and contiguous with said first recessed area, said second area being adapted to permit the trimming of the said medical device; and measuring means integrally disposed on the upper surface of said base longitudinally adjacent to the said first recessed area and laterally aligned in the same plane opposite to the said second recessed area;

whereby the medical device resting in the first recessed area can be cut to a selected measurement, the said second recessed area permitting a cutting instrument to cut through the medical device as it remains in place.

2. The container and surgical aid of claim 1 which further comprises:

a cover means including a lid adapted to fasten on the said base and enclose the said first and second recessed areas and the said medical device, said cover means being recessed complementarily to the first said recessed area so that, when closed, the lid will accommodate, enclose and hold in place the said medical device.

3. The container and surgical aid recited in claim 2 in which:

the said base comprises a platform disposed integrally adjacent to said recessed areas and enclosable within the said lid, whereby the said platform is maintained in sterile condition within the enclosed package and is adapted for surgical preparations for implantation of the said medical device.

4. The container and surgical aid recited in claim 3 in which:

the said cutting platform is integrally provided with measuring means whereby tissue being cut to size thereon can be precisely dimensioned.

5. In a container of the type used in total or partial replacement of middle ear ossicles, said container having a first recessed area in the base of said container and a complementary recessed area in a lid adapted to fit and enclose the prosthesis resting within the base, the improvement consisting of surgical supportive means comprising:

a second recessed area formed in the base coplanar with and adjacent to a portion of the first said recessed area, the said second recessed area being adapted to permit a cutting instrument to cut through the prosthesis resting in the said first recessed area; and measuring means integrally disposed on the surface of the base longitudinally adjacent the said first recessed area and laterally aligned opposite the said second recessed area whereby the cutting of the prosthesis can be determined in conformance to a determined measurement.

* * * * *

UNITED STATES PATENT AND TRADEMARK OFFICE
CERTIFICATE OF CORRECTION

PATENT NO. : 4,288,066
DATED : September 8, 1981
INVENTOR(S) : Harry T. Treace

It is certified that error appears in the above-identified patent and that said Letters Patent are hereby corrected as shown below:

On page 1 of the patent, in the ABSTRACT, right column, line 15, delete "apparatus" and substitute therefor --means--.

Signed and Sealed this

Third Day of November 1981

[SEAL]

Attest:

GERALD J. MOSSINGHOFF

Attesting Officer  Commissioner of Patents and Trademarks